United States Patent [19]

Rijke et al.

[11] Patent Number: 5,724,991
[45] Date of Patent: Mar. 10, 1998

[54] WRIST FIXATION DEVICE FOR ELBOW STRESS EXAMINATION

[76] Inventors: Arie M. Rijke, Rte. 10 Box 133, Charlottesville, Va. 22903; Henry T. Goitz, 22656 Wildwood, St. Clair Shores, W. Va. 48081

[21] Appl. No.: 550,578

[22] Filed: Oct. 31, 1995

Related U.S. Application Data

[63] Continuation-in-part of Ser. No. 19,602, Feb. 19, 1993, Pat. No. 5,462,068.

[51] Int. Cl.$^6$ ............................................. A61G 15/00
[52] U.S. Cl. ................................. 128/845; 128/881
[58] Field of Search ............................... 128/845, 846, 128/877, 878, 879, 881; 5/601, 623, 646, 647; 602/20, 21

[56] References Cited

U.S. PATENT DOCUMENTS

| | | | |
|---|---|---|---|
| 3,540,719 | 11/1970 | Romney | 5/647 |
| 4,082,257 | 4/1978 | Strickland | 5/647 |
| 5,136,743 | 8/1992 | Pirela-Cruz | 128/878 |

FOREIGN PATENT DOCUMENTS

| | | | |
|---|---|---|---|
| 2904785 | 8/1979 | Germany | 128/878 |

*Primary Examiner*—Michael A. Brown
*Attorney, Agent, or Firm*—Sheldon H. Parker

[57] ABSTRACT

The device is a diagnostic tool for the determination of the functional loss of the collateral ligaments of the elbow. The device serves to position and to stabilize the arm of a subject and to position the elbow in a predetermined fixed position to allow for X-raying of elbow joints under graded pressure. A first part of the device is a unit for receiving a hand and securing the wrist in a predetermined position. The hand receiving member has a planar upright support section which has a plurality of spaced holes. Preferably, the spaced holes are arranged in a plurality of parallel rows. The device includes a first rod shaped member or roller positioned in a hole such that it is contacted by the palm of the hand, with the palm upward in supination. The wrist is secured to a second rod or roller mounted in another of the holes, to hold the wrist in a predetermined position relative to the second roller. A third roller is provided such that the wrist is locked in position between the second and third rollers. Each of the plurality of hand securing rollers are positionable in the spaced holes so as to be adjustable relative to each other so as to receive a hand and wrist and to secure the hand and wrist in a predetermined supination position. A vertical post is provided for bracing the shoulder and a pressure mechanism applies pressure to the radiohumeral joint to elicit widening of the medial joint space.

6 Claims, 4 Drawing Sheets

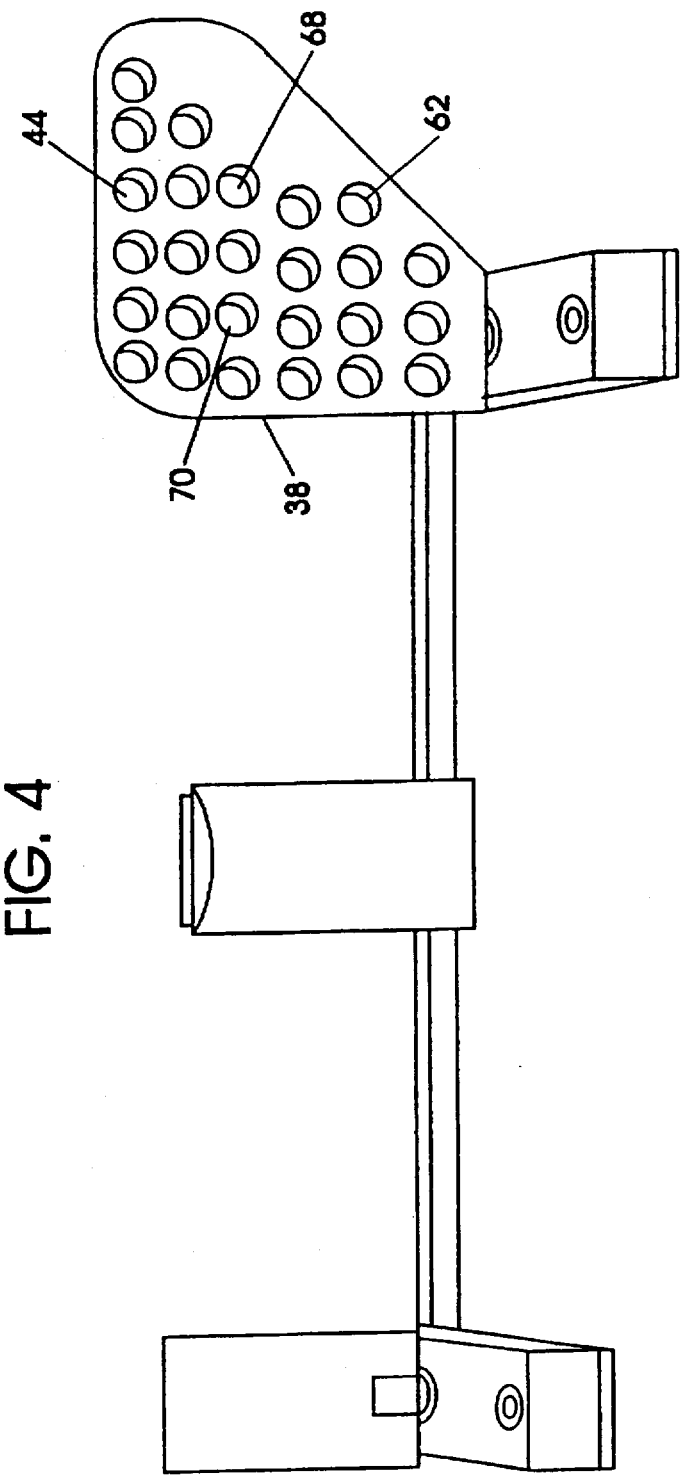

WRIST FIXATION DEVICE FOR ELBOW STRESS EXAMINATION

This application is a continuation-in-part of Ser. No. 08/019,602 filed Feb. 19, 1993, now U.S. Pat. No. 5,462,068 issued Oct. 31, 1995.

FIELD OF THE INVENTION

This invention relates generally to devices for securing and stabilizing the wrist in supination, for stress examination of the elbow ligaments.

BRIEF DESCRIPTION OF THE PRIOR ART

Sports injuries can be very painful and debilitating. Not all injuries, however, require surgery and many ligament injuries can be healed through rest and physical therapy. Determining the extent of the damage to ligaments allows the physician to evaluate whether or not surgery is required. The typical methods for evaluating damage to ligaments are magnetic resonance imaging (MRI), computerized axial tomography (CAT) scan and x-ray radiography. CT arthography relies on the presumed association of capsular extravasation of contrast with collateral ligament rupture. This method is unexplored and it is unknown whether reliable, consistent results can be obtained. Although MRI can directly image the affected ligament, it is unable to assess function properties. Both CT arthography and MRI techniques are high-cost and do not provide the reliability of the instant invention.

Devices are known for stabilizing a limb of the body for examination. As for example, U.S. Pat. No. 5,136,743 to Pirela-Cruz discloses a device for positioning the distal radiohumal joint (DRUJ) for medical examination. The Pirela-Cruz device allows stress to be applied to the radius and ulna to assess stability in the DRUJ and is especially useful for a CAT scans or X-rays. The Pirela-Cruz patent does not, however, place the hand in a supinated position but rather maintains the hand and wrist in a vertical position. This position does not place the wrist in supination, a requirement for stress examination of the elbow ligaments. Pirela-Cruz is concerned with the examination of the distal radioulnar joint and the primary concern is to immobilize the forearm against lengthwise movement.

U.S. Pat. No. 4,969,471 to Daniel et al., discloses a device which simultaneously measure mutually perpendicular linear displacements and angular displacements about an axis substantially perpendicular to the plane off the linear of the linear displacements. The Daniel et al device is particularly designed for use in connection with knee injuries.

U.S. Pat. No. 5,163,443 to Fry-Welch et al measures the forces which are applied by a limb and is useful for determining the presence of cumulative trauma disorders, such as carpal tunnel syndrome.

U.S. Pat. No. 3,715,587 to Burkhalter et al discloses instruments for performing in vivo analysis of bone mineral content by measuring the absorption of a scanning beam of monoenergetic photons.

U.S. Pat. No. 4,674,110, issued to Eaton et al places the hand in a pronated position for X-rays. The Eaton device is provided with a number of adjustment holes for receiving pegs to maintain the fingers in the desired position. The Eaton device does not, however, have the ability to place the hand in the supinated position required for examination of elbow ligaments.

The foregoing patents illustrated that there is a need for various devices to position limbs during analysis of injuries, as well as techniques to evaluate the injury. None of the prior art have addressed the problem of X-raying boney structures to reliably and reproducibly predict injury to ligaments. In the instant invention the extent of the injury can be quantitated non-invasively, particularly in the elbow area.

BRIEF DESCRIPTION OF THE DRAWING

FIG. 4 is a side view of the reverse side of FIG. 1; and

SUMMARY OF THE INVENTION

Figure 1:
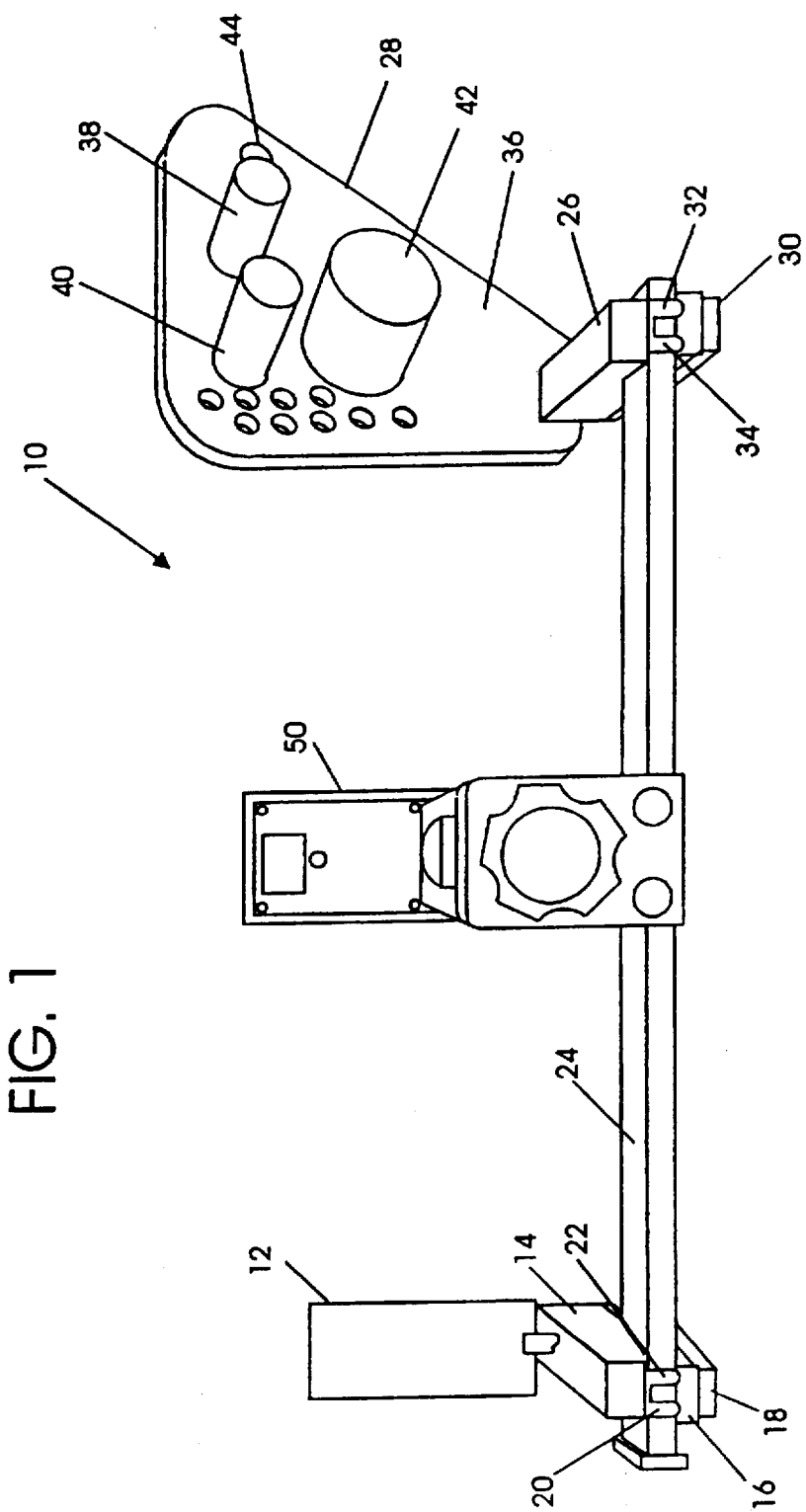
FIG. 1 is a side view of the instant invention.

A device of the present invention is employed as a diagnostic tool for the determination of the functional loss of the collateral ligaments of the elbow. The device serves to position and stabilizing the arm of a subject and to position the elbow in a predetermined fixed position to allow for X-raying of the elbow under graded pressure.

A first part of the device is a unit for receiving a hand and securing the wrist in a predetermined position. The hand receiving member has a planar upright support section which has a plurality of spaced holes. Preferably, the spaced holes are arranged in a plurality of parallel rows. The first part includes a first rod shaped member or roller positioned in a hole such that it is contacted by the palm of the hand, with the palm upward in a supine position. The wrist is secured to a second rod or roller mounted in another of the holes, to hold the wrist in a predetermined position relative to the second roller. In a preferred embodiment, a third roller is provided and the wrist is locked in position between the second and third rollers. Each of the roller members are dimensioned to be received in the spaced holes, such that they extend from the support section parallel to each other. The three rollers are located in the holes of the support member such that they are positioned at the apices of a triangle. Each roller has a resilient, tubular element enclosing at least a major portion of its length. Each of the plurality of hand securing rollers are positionable in the spaced holes so as to be adjustable relative to each other so as to receive a hand and wrist and to secure the hand and wrist in a predetermined supine position.

A second part of the device is a vertical post against which the shoulder is braced. The shoulder brace is rotatably supported on the carrier member, such that it is rotatably adjustable about a vertical axis.

A third part is a mechanism for applying pressure to the radiohumeral joint to elicit widening of the joint space. The third part is provided with a rotatable, threaded shaft. Rotation of the shaft causes a vertical portion of the third part to move relative to the elbow, thereby varying the degree of force being applied to the elbow. Also provided, is a device for reading the degree of force being applied to the joint. The third part is supported for movement normal to an imaginary first plane which includes the first and second parts of the device. By applying pressure to the radiohumeral joint widening of the medial elbow joint space is elicited.

The first part and the second part are positioned on the same side of the arm and the third part is positioned on the opposite side of the arm, such that movement of the third means in a direction normal to the first plane varies the pressure to the radiohumeral joint.

A carrier member is provided for adjustably retaining the first, second and third parts of the device. The carrier member is an elongated support element on which the three parts move relative to each other. Thus, the hand receiving member, the shoulder brace and the pressure mechanism are adjustably retained on the carrier member, and are spatially adjustable relative to each other to accommodate various arm lengths.

The procedure of the invention involves the determination of the functional loss of the collateral ligaments of the elbow, by (a) securing the wrist in a predetermined position, and maintaining the hand in a fixed position,
(b) bracing the shoulder against movement in a first direction,
(c) applying pressure in the first direction to the radiohumeral joint to elicit widening of the medial joint space while maintaining a predetermined flexion of elbow, and
(d) X-raying of boney structures of the elbow under graded pressure.

Preferably, the flexion of the elbow is on the order of about 25°.

In step (c) the pressure is applied in increments to the radiohumeral joint and in step (d) the incremental widening of the medial joint space is recorded by means of X-raying of the joint. The functional loss of the collateral ligaments of the elbow is based on the relationship between the widening and the applied pressures.

DETAILED DESCRIPTION OF THE INVENTION

The instant invention discloses a device which allows for the elbow to be placed in a fixed position to allow for ligament X-rays under graded pressure. Increased pressure is applied to the radiohumeral joint to elicit widening of the medial joint space, with each increment of pressure being recorded on X-ray film. Recording the widening of the medial joint space allows for the determination of the functional loss of the collateral ligaments of the elbow based on the relationship between the widening and the applied pressures. By way of contrast, prior diagnostic systems were restricted to the gravity valgus test, that used the weight of the forearm to provoke ulnohumeral subluxation.

The wrist fixation device of the present invention stabilizes the wrist in supination, a requirement for stress examination of the elbow ligaments. The vertical, planar member supports a plurality of bars, preferably foam rubber covered, which can be placed in a variety of relative positions. The fingers clasp the distal roller bar, such that the volar aspect of the wrist is secured to the proximal roller bar by Velcro straps, or other means, or otherwise held in a fixed position, as for example, additional roller bars.

The definitions of supination for incorporation into this disclosure are taken from *The American Heritage Dictionary and Dorland's Illustrated Medical Dictionary*. Due to the criticality of hand and wrist positioning, the following dictionary definitions of supine are incorporated herein in order to eliminate any confusion.

"su*pine (sUU-pIn', sUU'pIn') adj.
1. Lying on the back or having the face upward. See Synonyms at prone.
2. Having the palm upward. Used of the hand.
3. Marked by or showing lethargy, passivity, or blameworthy indifference. See Synonyms at inactive.
4. Inclined; sloping.

*The American Heritage Dictionary*, Houghton Mifflin Company, Boston, Mass. (1992).

"supination . . . Applied to the hand, the act of turning the palm forward (anteriorly) or upward, performed by the lateral rotation of the forearm."

*Dorland's Illustrated Medical Dictionary*, W. B. Saunders Co., Philadelphia, Pa. (1988).

FIG. 1 illustrates a side view of the positioning device 10. The shoulder brace 12 is affixed at right angles to the slide brace 14 and provides the "set point" for positioning the arm. The shoulder brace 12 can be manufactured to slide within the slide brace 14, however little benefit would be derived from this as the positioning device 10 inherently allows for variations in arm size. The slide brace 14 is manufactured with a notched area dimensioned to receive the slide bar 24. Pegs 20 and 22 lock the slide bar 24 into the notched portion of the slide brace 14. A non-slip rubber base 18 to prevents the positioning device 10 from moving while in use. A second slide brace 26 is maintains the other end of the slide bar 24 parallel, with the slide bar 24 being locked into position through use of pegs 32 and 34. The slide brace 26 also has a non-slip rubber base 30. An adjustable pressure unit 50 is mounted on the slide bar 24 to move along the slide bar 24, allowing for accurate positioning of the pressure unit 50 over the radiohumeral joint. The slide braces 14 and 26, slide bar 24 and the pressure unit 50 are manufactured by Telos Company and have been used for cruciate ligament testing.

The adjustable wrist fixation panel 28 is affixed to the slide brace 26, on the same plane as the shoulder brace 12. The adjustable wrist fixation panel 28 illustrated herein is a trapezoidal shape, however this is a preferred configuration and should not be considered to limit the instant disclosure. The narrow portion of the adjustable wrist fixation panel 28 is affixed to the slide brace 26. The illustrated adjustable wrist fixation panel 28 is predrilled with parallel rows of receiving holes 44 to provide for adjustability. The distal roller bar 38 is a foam covered roller bar which has one end dimensioned to fit through the receiving holes 44, lock the distal roller bar 38 into the adjustable wrist fixation panel 28. The proximal roller bar 40 is manufactured identical to the distal roller bar 38 and is also locked into the adjustable wrist fixation panel 28. The distal roller bar 38 and the proximal roller bar 40 are interchangeable from a manufacturing purpose, however they have been referred to separately herein for clarification. The distal roller bar 38 and proximal roller bar 40 are positioned on the adjustable wrist fixation panel 28, in conjunction with the wrist brace 42, to lock the wrist in supination. The ability to keep the wrist in a supination is critical so that a reproducible anterior-posterior position of the elbow with respect the direction of the X-ray beam is maintained and rotation is avoided. The reproducibility of the positioning of the elbow, in essence, means that a desired predetermined position of the elbow will be attained through the method and apparatus of the invention. In addition, wrist supination is thought to help decrease muscle splintering by the flexor capri ulnaris-radialis muscles.

The fixation panel 28, as illustrated, is drilled with receiving holes 44 in a predetermined pattern. Other means, such as U-brackets, screws, etc., can be used for locking the roller bars into place. Further, the pattern illustrated herein is only one which will be effective for positioning the wrist in the desired position. The configuration illustrated herein provides the greatest adjustability for the least cost, however other designs can be readily incorporated. The fixation panel must lock the wrist in supination and be able to provide a reproducibility to the position.

The patient's shoulder is placed against the restraining panel 12 with the elbow flexed 25° and resting on or near the x-ray film cassette. The wrist is placed to rest on the wrist brace 42 and the proximal roller bar 40 is positioned at the volar portion of the wrist to lock the wrist in position the desired position. The distal roller bar 38 is positioned to allow the patient's fingers to close around the distal roller bar 38. The receiving holes 44 allow for the distal roller bar 38, proximal roller bar 40 and the wrist brace 42 to be positioned to maintain the a 25° flexion of the elbow so as to unlock the humeral-olecranon joint. The pressure unit 50 is placed adjacent to the radiohumeral joint and pressure is applied to the joint, as shown in FIG. 2.

Figure 2:
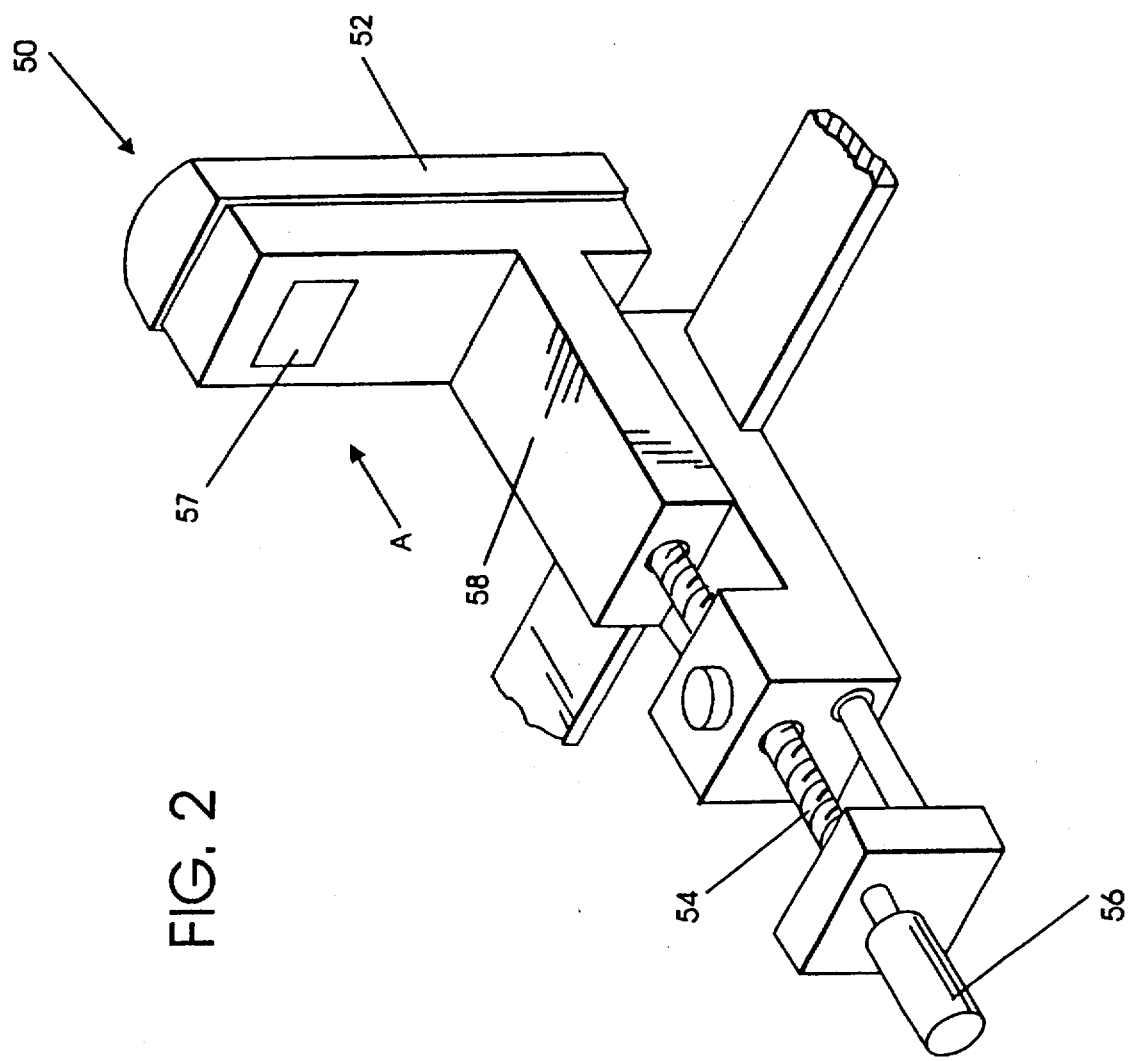
FIG. 2 is a perspective view of the instant invention in use.

FIG. 2 illustrates the pressure unit 50 in a position to apply pressure to the radiohumeral joint. The threaded screw 54 extends through the pressure unit 50 and has a rotatable handle 56 at one end and is connected to the pressure panel base 58 at the other end. As the rotatable handle 56 is turned in one direction, the threaded screw 54 is removed from the pressure panel base 58, forcing the pressure panel base 58 in the direction of Arrow A. The pressure panel 52 is in contact with the patient's elbow prior to the application of pressure. As the pressure panel base 58 extends toward the patient's elbow, pressure is applied through the pressure panel 52 to the radiohumeral joint. A digital numeral display 57 indicates the amount of pressure applied to the joint. After each increased increment of pressure, an x-ray is taken of the joint.

Figure 3:
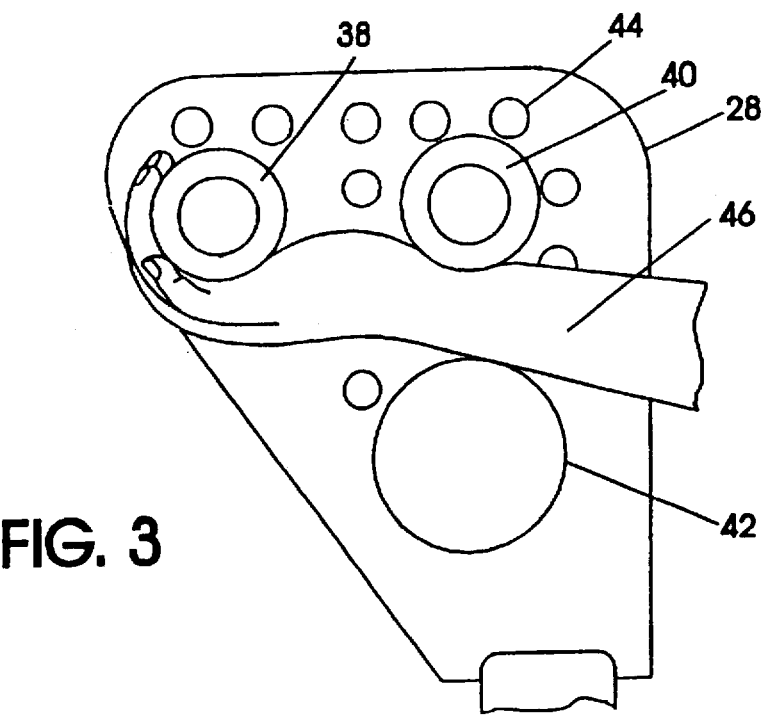
FIG. 3 is a side view of the adjustable panel of the instant invention.

FIG. 3 illustrates a detailed view of the adjustable wrist fixation panel 28 with the distal roller bar 38, proximal roller bar 40 and wrist brace 42 inserted into the receiving holes 44. The patient's arm 46 has been placed in the appropriate position for examination. The receiving holes 44 are pre-drilled into the adjustable wrist fixation panel 28 in a predetermined, desired pattern. The patient's hand grips the distal roller bar 38 and the proximal roller bar 40 and wrist brace 42 locks the forearm in a position to maintain the wrist in supination. In the illustration herein, the receiving holes 44 are drilled in rows of varying length. This is presented as an example of the configuration and should not be considered as a limitation. It is critical, however, that a sufficient number of receiving holes 44 be provided to allow for maximum adjustability. As an alternative to use of the proximal roller bar 40, the wrist brace 42 can be provided with Velcro® straps to affix the wrist in place.

Figure 5:
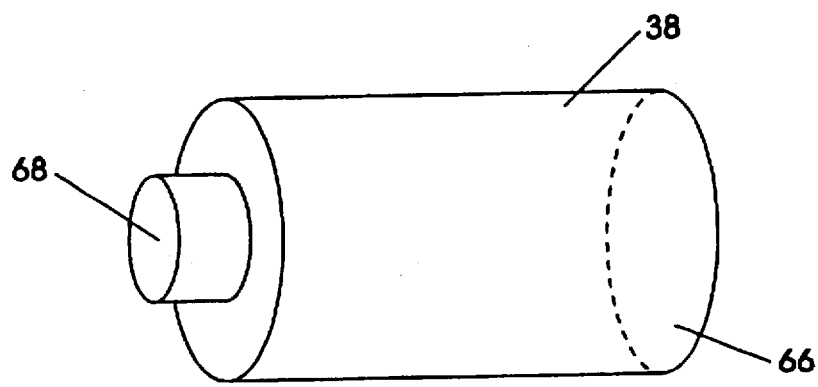
FIG. 5 is a perspective view of the grips of the instant invention.

FIG. 4 illustrates the reversed side of FIG. 1, illustrating one method of inserting the distal roller bar 38, proximal roller bar 40 and wrist brace 42. The distal roller bar 38, illustrated in FIG. 5, is a foam covered support bar 68, a portion of which extends beyond the foam 66. It is not necessary for the bars 38, 40 and 42 to be provided with foam 66, however due to the increase comfort level for the patient, it is preferable. Although the diameter of the roller bars 38, 40 and 42 is not narrowly critical, the diameter should be such to provide comfort and support. It is preferable that the distal roller bar 38 have a diameter which allows for the bar 38 to be gripped by the user. The bar 68 is dimensioned for a friction fit into the receiving holes 44. As an alternative design, the portion of the bar 68 covered by foam 66 can have an increased diameter. The portion of the bar 68 which extends into the receiving holes 44 should be approximately equal to the depth of the receiving holes 44 to prevent tilting or breakage when pressure is applied. Various additional methods known to those versed in the prior art can be used to lock the bar 68 into the adjustable wrist fixation panel 28.

The wrist fixation panel 28 of the instant invention, as illustrated herein, is affixed to slide brace 26 to interact with the slide bar 24. Although the illustrated design is convenient for this application, other applications may require the wrist fixation panel to interact with other equipment. The base utilized with the wrist fixation panel is not critical to the use of the panel and can be any design which appropriately interacts with the equipment used. In instances where the moveability of the fixation panel is not important, the base can be permanently secured to a table.

The instant device provides a heretofore unavailable method for repeatedly positioning the wrist in a supinated position for the examination of elbow ligaments. The positioning and maintaining the wrist in the supine position is critical to accurate evaluation of the damage to the elbow. Further, the exact repeatability of the position allows for progress to be monitored during treatment.

What is claimed is:

1. A device for positioning a patient's elbow for examination during a diagnostic procedure, by reproducibly positioning said patient's wrist, in a predetermined supine position relative to said patient's body, said body being in a vertical plane, said device comprising:

a) a support member, said support member being in said vertical plane and positioned to receive securing means to maintain said wrist in a predetermined supine position by placing said patient's palm in a horizontal plane, said horizontal plane being horizontal relative to said vertical plane, said support member having multiple receiving means, said multiple receiving means being spaced at predetermined distances from one another and providing horizontal and vertical adjustability for said securing means;

b) securing means for receiving and securing said patient's palm and wrist in said supine position, said securing means being carried in said horizontal plane by said multiple receiving means and including;

i) a first wrist retaining member, said first wrist retaining member extending normal from said support member and repositioned, within said multiple receiving means, to contact said patient's palm in said horizontal plane, ii) a second wrist retaining member, said second wrist retaining member extending normal from said support member and repositionable, within said multiple receiving means, to contact the posterior portion of said patient's wrist, and iii) wrist securing member to secure said wrist in said predetermined supine position;

c) base connection means, said base connection means connecting said support member to a base surface, said base surface being at substantially right angles to said support member, whereby securing said patient's wrist in said supine position in said horizontal plane positions said patient's elbow to elicit widening of the medial joint space.

2. The device of claim 1, wherein said wrist securing member is a releasable, self-adhering strap member.

3. The device of claim 1, wherein said wrist securing member is a third member extending in said second plane from said vertical support member, said second wrist retaining member and said wrist securing member being repositionable, within said multiple receiving means, for each patient in order to position said second wrist retaining member in firm contact with the anterior of said wrist and said wrist securing member in firm contact with the posterior of said wrist, said first wrist retaining member, said second wrist retaining member and said wrist securing member being at the vertexes of a triangle, whereby said wrist is fixed in a predetermined supine position within said horizontal plane.

4. The device of claim 1, wherein each of said first wrist retaining member, said second wrist retaining member and said wrist securing member is substantially rod shaped, and further comprise a resilient tubular cover member on each of said members.

5. The device of claim 1 wherein said multiple receiving means are openings within said support member to carry said securing means.

6. The method of reproducibly positioning a patient's wrist in supination during a diagnostic procedure by unlocking the patient's olecranon from its bony socket, comprising:

a) placing a patient's wrist proximate a vertical support member, said support member and said patient's shoulder being in substantially the same vertical plane to maintain said wrist in a predetermined supine position and the arm essentially in line with said shoulder;

b) securing said patient's hand and wrist in said supine position to said support member by a securing means, said securing means including;

i) a first wrist retaining member extending normal from said support member and positioned to be contacted by the palm of the hand, said first wrist retaining member having a length approximately equal to the width of a patient's palm, ii) a second wrist retaining member extending from said support member and positioned to be contacted by the posterior portion of the wrist, said second wrist retaining member having a length approximately equal to the width of a patient's wrist, and iii) wrist securing member to secure said wrist in said predetermined supine position relative to a base member, c) maintaining said wrist in a position essentially horizontal, d) adjusting said support member along said base member to place said patient's elbow at approximately a 25° flexion, whereby maintaining said patient's wrist in a supine position with said elbow at said approximately a 25° flexion, unlocks the patient's olecranon from its bony socket.

\* \* \* \* \*